United States Patent [19]
Friedman et al.

[11] Patent Number: 6,039,895
[45] Date of Patent: Mar. 21, 2000

[54] BENZOQUINONEIMINES AS VINYL AROMATIC POLYMERIZATION INHIBITORS

[76] Inventors: Howard Stephen Friedman, 150 Forest Hill Rd., North Haven, Conn. 06473; Paul Edwin Stott, 20 Clearview Dr., Sandy Hook, Conn. 06482

[21] Appl. No.: 08/276,685

[22] Filed: Jul. 18, 1994

Related U.S. Application Data

[63] Continuation of application No. 08/053,958, Apr. 27, 1993, abandoned, which is a continuation of application No. 07/600,056, Oct. 18, 1990, abandoned.

[51] Int. Cl.⁷ .................................................. C09K 15/00
[52] U.S. Cl. ........................ 252/404; 252/401; 252/402; 552/303; 564/276; 564/306; 570/200
[58] Field of Search ................... 252/401, 402, 252/404; 564/276, 306; 570/200; 552/303

[56] References Cited

U.S. PATENT DOCUMENTS

| | | | |
|---|---|---|---|
| 2,526,567 | 7/1950 | Drake et al. | 202/57 |
| 3,004,042 | 10/1961 | Coppinger et al. | 552/302 |
| 3,929,404 | 12/1975 | Kalopissis et al. | 564/276 |
| 4,105,506 | 8/1978 | Watson | 203/9 |
| 4,457,806 | 7/1984 | Grivas et al. | 203/9 |
| 4,466,905 | 8/1984 | Butler et al. | 252/403 |
| 4,633,026 | 12/1986 | Kolich | 570/200 |
| 4,692,544 | 9/1987 | Goerner et al. | 560/4 |
| 4,915,873 | 4/1990 | Abruscato et al. | 252/402 |

FOREIGN PATENT DOCUMENTS

| | | |
|---|---|---|
| 0158512 | 11/1986 | India . |
| 2159826 | 12/1985 | United Kingdom . |

OTHER PUBLICATIONS

Nigam et al., CA 107: 116131 a (Abstract Only).
Taimr et al. CA 108: 133138 w (Abstract Only).
PCT International Application No. PCT/US 91/07188 Search Report, 1992.

*Primary Examiner*—Shailendra Kumar
*Attorney, Agent, or Firm*—Raymond D. Thompson

[57] ABSTRACT

This invention relates to a vinyl aromatic, especially styrene, polymerization inhibitor system comprising an N-phenyl-1,4-benzoquinoneimine compound and optionally an aryl-substituted phenylenediamine.

10 Claims, No Drawings

BENZOQUINONEIMINES AS VINYL AROMATIC POLYMERIZATION INHIBITORS

This is a continuation of prior complete application U.S. application Ser. No. 08/053,958 filed Apr. 27th, 1993, abandoned, which is a continuation of application Ser. No. 07/600,056, filed Oct. 18, 1990, now abandoned.

FIELD OF THE INVENTION

This invention is directed to a polymerization inhibitor system for vinyl aromatic compounds comprising (a) an N-phenyl-1,4-benzoquinoneimine compound; and, optionally, (b) an aryl-substituted phenylenediamine compound. In other aspects, this invention is directed to a vinyl aromatic composition stabilized against polymerization by such polymerization inhibitor system, as well as to a method of stabilizing a vinyl aromatic composition against polymerization which method comprises adding an effective amount of such polymerization inhibitor system.

BACKGROUND OF THE INVENTION

Commercial processes for the manufacture of vinyl aromatic compounds such as monomeric styrene, divinyl benzene and lower alkylated styrenes (such as alpha-methylstyrene and vinyltoluene) typically produce products contaminated with various impurities, such as benzene, toluene and the like. These impurities must be removed in order for the monomer product to be suitable for most applications. Such purification of vinyl aromatic compounds is generally accomplished by distillation.

However, it is well known that vinyl aromatic compounds polymerize readily and that the rate of polymerization increases rapidly as the temperature increases. In order to prevent polymerization of the vinyl aromatic monomer under distillation conditions various polymerization inhibitors have been employed.

In general, the compounds which are commercially employed as such polymerization inhibitors are of the dinitrophenolic class. Thus, for example, Drake et al, in U.S. Pat. No. 2,526,567, show the stabilization of nuclear chlorostyrenes employing 2,6-dinitrophenols. Similarly, U.S. Pat. No. 4,105,506, to Watson, discloses the use of 2,6-dinitro-p-cresol as a polymerization inhibitor for vinyl aromatic compounds.

In addition, it has been disclosed by Butler et al, in U.S. Pat. No. 4,466,905, that, in the presence of oxygen, phenylenediamines in the distillation column together with 2,6-dinitro-p-cresol will reduce the amount of polymerization which occurs.

While dinitrophenols are effective polymerization inhibitors, there are several disadvantages associated with their use, either alone or in blends. For example, dinitrophenols are solids that, if subjected to temperatures above their melting points, are unstable and may explode (see U.S. Pat. No. 4,457,806). Moreover, dinitrophenols are highly toxic, many having a dermal $LD_{50}$ (rabbit) in ethylbenzene of less than 2 g/Kg.

While such prior art inhibitors may inhibit the polymerization of vinyl aromatic compounds to some degree, it would be desirable to possess polymerization inhibitors which would more effectively delay the onset of polymerization and/or which would avoid the use of highly toxic compounds such as dinitrophenols.

Recently, it has been disclosed by Kolich, in U.S. Pat. No. 4,633,026, that halogenated vinyl aromatic compounds (such as bromostyrene) may be inhibited from polymerizing by the addition of an amine polymerization inhibitor selected from the group consisting of certain alkyl-substituted phenylenediamine compounds and phenothiazine compounds in the presence of air.

More recently, Abruscato et al in U.S. Pat. No. 4,774,374 discloses using a vinyl aromatic compound along with an oxygenated phenylenediamine for polymerization inhibition in vinyl aromatic species. In U.S. Pat. No. 4,915,873 Abruscato shows vinyl aromatic compounds stabilized against polymerization using an effective amount of a phenothiazine compound and an aryl-substituted phenylenediamine. Although these inventions do not utilize dinitrophenols, the inhibitors of these inventions require air to function.

Accordingly, it is an object of this invention to provide an improved polymerization inhibitor system for the prevention of polymerization of vinyl aromatic compounds.

It is an additional object of this invention to provide an inhibitor system for the prevention of polymerization of vinyl aromatic compounds, which inhibitor system does not comprise toxic dinitrophenolic compounds.

Another object of this invention is to provide a vinyl aromatic polymerization inhibitor sytem which does not require air to function.

It is a further object of this invention to provide a vinyl aromatic composition which is stabilized against polymerization.

It is yet another object of this invention to provide an improved method for inhibiting the polymerization of vinyl aromatic compounds.

The foregoing and additional objects will become more fully apparent from the following description and accompanying Examples.

DETAILED DESCRIPTION OF THE INVENTION

In one aspect, this invention is directed to a vinyl aromatic polymerization inhibitor system comprising:

an N-phenyl-1,4-benzoquinoneimine compound having the formula I

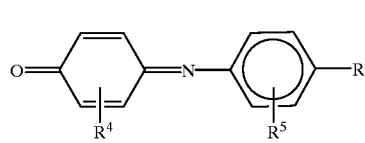

wherein R is H; $NR^1R^2$ wherein $R^1$ and $R^2$ are independently selected from the group consisting of hydrogen, $C_1$–$C_8$ alkyl, $C_6$–$C_{10}$ aryl, $C_7$–$C_{16}$ alkaryl and $C_3$–$C_8$ cycloalkyl; or $OR^3$ wherein $R^3$ is hydrogen, $C_4$–$C_8$ cycloalkyl or $C_1$–$C_8$ alkyl; and $R^4$ and $R^5$ are independently selected from the group consisting of hydrogen, $C_1$–$C_8$ alkyl, $C_4$–$C_8$ cycloalkyl, $C_6$–$C_{10}$ aryl, and $C_7$–$C_{16}$ alkaryl.

In another aspect, this invention is directed to a polymerization inhibitor system comprising:

a) an N-phenyl-1,4-benzoquinoneimine having the structure and above-identified substituents of formula I; and b) a phenylenediamine of formula II

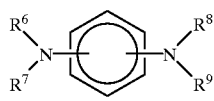

II wherein $R^6$ is $C_6$–$C_{10}$ aryl or $C_7$–$C_{16}$ alkaryl; and $R^7$, $R^8$ and $R^9$ are independently selected from the group consisting of hydrogen, $C_1$–$C_{12}$ alkyl, $C_3$–$C_{12}$ cycloalkyl, $C_7$–$C_{11}$, aralkyl and $C_7$–$C_{16}$ alkaryl.

In still a further aspect, this invention is directed to a vinyl aromatic composition stabilized against polymerization, said composition comprising a vinyl aromatic compound together with a benzoquinoneimine compound of formula I and optionally, a phenylenediamine of formula II. In yet another aspect, this invention is directed to a method for inhibiting the polymerization of vinyl aromatic compounds, which method comprises blending a polymerization inhibiting effective amount of the stabilization system of this invention to the vinyl aromatic to be stabilized.

Particularly suitable N-phenyl-1,4-benzoquinoneimines of formula I which can be employed herein are those wherein $R^4$ and $R^5$ are hydrogen and $R^1$ is $C_1$–$C_8$ alkyl. A more preferred benzoquinoneimine is where $R^4$ and $R^5$ are hydrogen and $R^1$ and $R^2$ are methyl, i.e.,

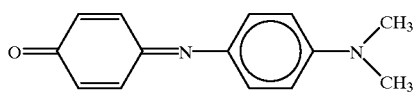

III

The compound of formula III is commercially available for example, from the Aldrich Chemical Company, Milwaukee, Wis. and is known as phenol blue. Phenol blue is a known oxidation-reduction indicator, as is discussed in *Oxidation-Reduction Potentials of Organic Systems*, Williams and Watkins Press, 1960., by W. M. Clark.

Other published uses for phenol blue include its use as a reactant in organic complexing reactions(Menger et al in *J. Am. Chem. Soc.*, 103(19) 5938 in 1981), and its use as an anti-tumor agent (Hodnett et al., *J. Biol. Phys*, 5(1–2), 24–48, 1977).

Another preferred compound of this benzoquinoneimine class is indophenol, whose structure is

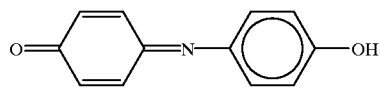

IV

Indophenol has long been used to synthesize sulfur dyes. More recently, indophenol has been used on an anti-tumor agent, (CHEM. ABSTRS. 107(7):51493y and 97(21): 174475b) and as a deactivator in water-splitting systems of photosynthesis.

Similarly, compounds such as N-phenyl-1,4-benzoquinoneimine

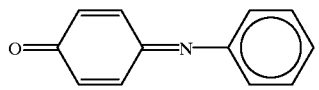

V have been reported to functions as polymer antidegradants and stabilizers by trapping organic radicals [Taimr et al., *Die Angewandte Makromolekulare Chemie*, 175, 169–180 (1990)]. The phenylenediamine component of the inhibitory blends of this invention, which is optionally present, is of the formula II above. Preferred compounds include those wherein the amine groups are in the para position. Particularly preferred compounds are the para-phenylenediamines wherein $R^7$ and $R^8$ are hydrogen; $R^6$ is phenyl; and $R^9$ is $C_3$–$C_8$ alkyl or $C_3$–$C_8$ cycloalkyl.

Illustrative of the preferred phenylenediamine compounds which may be employed include N-phenyl-N'-isopropyl-p-phenylenediamine, N-phenyl-N'-(1,3-dimethylbutyl)-p-phenylenediamine, N-phenyl-N'-(1,4-dimethylpentyl)-p-phenylenediamine and N-phenyl-N'-cyclohexyl-p-phenylenediamine. Moreover, mixtures of phenylenediamine compounds may also be employed. The phenylenediamine compounds may be of the oxygenated species as described in U.S. Pat. No. 4,774,374 to Abruscato et al.

An important advantage of this invention over what is known in the art is that the polymerization inhibitors do not need air to function. In, for example, U.S. Pat. No. 4,774,374, the polymerization inhibitors and the processes for their use require air or oxygen to function. As illustrated by the following examples, the presence of air may add to the efficacy of the inhibitors of the present invention, but air or oxygen is not required. Manufacturers of vinyl aromatic compounds, such as styrene, prefer to distill said compounds under vacuum, i. e., without air, for operating outside of the explosive envelope is obviously safer. Thus, the stabilizer compositions of the instant invention provide a much desired advantage to these vinyl aromatic compound manufacturers.

Additionally, the N-phenyl-1,4-benzoquinoneimines and blends therewith in ethylbenzene of this invention have dermal $LD_{50}$ (rabbit) values of greater than 2 g/kg. The dermal $LD_{50}$ (rabbit) in ethylbenzene values of dinitrophenol: phenylenediamine blends can be said to be "relatively non-toxic" but obviously the dinitrophenol component cannot be so labelled. Both components of the blends of this invention, however, can be labelled "relatively non-toxic".

The N-phenyl-1,4-benzoquinoneimines and the phenylenediamine compounds of this inventions are generally employed in weight ratios of between about 10:1 and about 1:10. Preferably, weight ratios of between about 4:1 and about 1:4 are employed, with ratios of between about 2:1 and about 1:2 being particularly preferred.

The polymerization inhibitor compositions of this invention may further comprise an aromatic hydrocarbon solvent. Illustrative of such solvents are benzene, toluene, xylene, ethylbenzene and other alkyl-benzenes as well as vinyl aromatic compounds themselves such as styrene, alpha-methylstyrene and the like. Typically, when solvents are employed the hydrogenated precursors of the vinyl aromatic to be stabilized are the preferred solvents. Thus, for the stabilization of styrene, ethylbenzene is the preferred solvent. Similarly for the stabilization of alpha-methylstyrene, isopropylbenzene is the preferred solvent.

Illustrative of the vinyl aromatic compounds which may be stabilized against polymerization by the process of this invention are styrene, alpha-methylstyrene, vinyltoluene and divinylbenzene, as well as halogenated species thereof.

The stabilized vinyl aromatic composition of this invention may be in the form of a reaction mixture additionally comprising the starting materials of the vinyl aromatic compound to be stabilized as well as by-products of the production process. Thus, in the case of styrene, the reaction mixture will typically include starting materials such as benzene, ethylbenzene and ethylene, as well as by-products such as diethylbenzene, vinyl toluene and the like.

The primary use of the polymerization inhibitor systems of this invention is to prevent the polymerization of vinyl aromatics during purification and/or distillation to remove unreacted starting materials and distillable by-products. Typically, this involves the sequential distillation of the vinyl aromatic reaction product through a plurality of distillation columns. In the first of such columns, a relatively large amount of starting material and by-products will be present, while in the last column essentially pure vinyl aromatic compound (plus polymerization inhibitors and heavy, nondistillable byproducts) will be present.

The method of this invention involves adding to a vinyl aromatic compound an effective amount of the "instant polymerization inhibitor system." When the polymerization inhibitor system of this invention is employed during the purification and/or distillation of vinyl aromatic compounds, it is preferred that oxygen, whether in the form of air or otherwise, be present. It is also noted that the polymerization inhibitor system of this invention will be effective for uses other than during distillation, e.g., during the shipment or storage of vinyl aromatic compounds.

The methods of this invention comprise the addition to a vinyl aromatic composition of an effective amount of the instant polymerization inhibitor system. As employed herein, the term "effective amount" refers to that amount of inhibitor which is needed to prevent the formation of more than about 1 weight percent of vinyl aromatic polymer in less than about 3 hours at temperatures of between about 90° C. and about 150° C. Although the amount of polymerization inhibitor required will vary somewhat (based upon such factors as the particular vinyl aromatic compound stabilized; the particular benzoquinoneimine and phenylenediamine species employed; and the like) such an effective amount may be readily determined by routine experimentation. In general, such an effective amount will be between about 50 and about 1,500 parts per million by weight of vinyl aromatic compound.

The polymerization inhibitor system of this invention will provide stability against vinyl aromatic polymerization at temperatures typically employed for the purification of vinyl aromatic compounds (i.e., from about 90° to about 140° C.) for periods well in excess of those typically employed for such purification. This stability is achieved without the use of undesirably toxic dinitrophenolic compounds which are generally employed in commercial operations today.

EXAMPLES 1–16

To a fifty milliliter flask charged with forty grams of styrene were added the various amounts and types of inhibitors as indicated in Tables 1 and 2 below. The inhibitors tested include phenol blue (PB), N-(1,4-Dimethyl Pentyl)-N'-phenyl-p-phenylenediamine (I-3), and PB:I-3 blends.

The flask was fitted with a magnetic stirrer and septum closure with a syringe needle as a vent and heated in an oil bath to 118° C. (plus or minus 2° C.). The flask was purged with approximately 5 cc/min of air or nitrogen passed beneath the liquid surface during the period of the test. During the test period, samples were removed from the flask periodically and tested for degree of polymerization by measuring the changes in refractive index. The time until onset of polymerization which is defined as the point at which one (1) weight percent of the styrene had polymerized, was determined in each example and tabulated below.

In order to compare these results with prior art vinyl aromatic polymerization inhibitors, experiments were run in an identical manner to those described above utilizing dinitro-p-cresol (DNPC). These experiments were conducted both in air and nitrogen atmospheres at 50, 100, 200, and 400 ppm, as shown in Tables 1 and 2 below.

TABLE I (Nitrogen Atmosphere)

| Example | Inhibitor or Blend | Dosage* (ppm) | Induction Time** (minutes) |
|---|---|---|---|
| A | DNPC | 100 | 70 |
| B | I-3 | 50 | 13 |
| C | I-3 | 100 | 17 |
| 1 | PB | 50 | 45 |
| 2 | PB | 100 | 46 |
| 3 | PB | 200 | 45 |
| 4 | PB | 400 | 50 |
| 5 | PB:1–3 | 50 | 45 |
| 6 | PB:1–3 | 100 | 54 |
| 7 | PB:1–3 | 200 | 67 |
| 8 | PB:1–3 | 400 | 71 |

TABLE 2

(Air)

| Example | --Inhibitor or Blend | Dosage (ppm) | Induction Time (minutes)-- |
|---|---|---|---|
| D | DNPC | 100 | 60 |
| E | I-3 | 50 | 119 |
| F | I-3 | 100 | 285 |
| 9 | PB | 50 | 210 |
| 10 | PB | 100 | 285 |
| 11 | PB | 200 | 420+ |
| 12 | PB | 400 | 420+ |
| 13 | PB:I-3 | 50 | 195 |
| 14 | PB:I-3 | 100 | 325+ |
| 15 | PB:I-3 | 200 | 420+ |
| 16 | PB:I-3 | 400 | 420+ |

Notes for Tables 1 and 2:
*The blends always use equal weight amounts of the two components.
**The tests were stopped after 7 hours (420 minutes) due to the limitations of the work-day.

The data in Table 1 indicates that longer induction times occurred in nitrogen for the PB:I-3 blends. Also shown is that the induction times for PB alone are longer than those for I-3 alone. Furthermore, the induction times even in the absence of air or oxygen for the non-toxic blends of the instant invention can be made equivalent to the induction times for the industry standard, DNPC, which is known as a highly toxic compound.

In the presence of air (Table 2) the induction times for all the polymerization inhibitors are longer than in nitrogen. It is shown that I-3 alone has longer induction times than DNPC alone. The induction times for PB and PB:I-3 blends are much longer, and in fact serendipitously show an unexpected degree of polymerization inhibition over those of the comparative examples. The data indicates that in the presence of air, unexpected synergism exists when phenol blue and a phenylenediamine of this invention are combined as vinyl aromatic polymerization inhibitors.

The above embodiments and examples illustrate the scope and spirit of the instant invention. These embodiments and examples will make apparent to those skilled in the art, other embodiments and examples within the scope of the present invention. Therefore, the instant invention should be limited only by the appended claims.

What is claimed is:

1. A polymerization inhibitor system comprising an N-phenyl-1,4-benzoquinoneimine compound having the formula:

$$\text{I}$$

wherein R is $NR^1R^2$; wherein $R^1$ is $C_1$–$C_8$ alkyl and $R^2$ is selected from the group consisting of hydrogen, $C_1$–$C_8$ alkyl, $C_6$–$C_{10}$ aryl, $C_7$–$C_{16}$ alkaryl and $C_3$–$C_8$ cycloalkyl; and $R^4$ and $R^5$ are independently selected from the group consisting of hydrogen, $C_1$–$C_8$ alkyl, $C_4$–$C_8$ cycloalkyl, $C_6$–$C_{10}$ aryl and $C_7$–$C_{16}$ alkaryl.

2. A polymerization inhibitor system comprising:
   (a) an N-phenyl-1,4-benzoquinoneimine compound of formula I:

$$\text{I}$$

wherein R is $NR^1R^2$; wherein $R^1$ is $C_1$–$C_8$ alkyl and $R^2$ is selected from the group consisting of hydrogen, $C_1$–$C_8$ alkyl, $C_6$–$C_{10}$ aryl, $C_7$–$C_{16}$ alkaryl and $C_3$–$C_8$ cycloalkyl; and $R^4$ and $R^5$ are independently selected from the group consisting of hydrogen, $C_1$–$C_8$ alkyl, $C_4$–$C_8$ cycloalkyl, $C_6$–$C_{10}$ aryl and $C_7$–$C_{16}$ alkaryl; and
   (b) a phenylenediamine of formula II $$\text{II}$$

wherein $R^6$ is $C_6$–$C_{10}$ aryl or $C_7$–$C_{16}$ alkaryl; and $R^7$, $R^8$ and $R^9$ are independent selected from the group consisting of hydrogen, $C_1$–$C_{12}$ alkyl, $C_3$–$C_{12}$ cycloalkyl, $C_7$–$C_{11}$ aralkyl and $C_7$–$C_{16}$ alkaryl.

3. The polymerization inhibitor system of claim 2 wherein $R^1$ and $R^2$ are $CH_3$; and $R^4$ and $R^5$ are hydrogen.

4. The polymerization inhibitor system of claim 2 wherein $R^4$ and $R^5$ are hydrogen.

5. The polymerization inhibitor system of claim 2 wherein $R^4$ and $R^5$ are hydrogen.

6. The polymerization inhibitor system composition of claim 2 wherein $R^4$ and $R^5$ are hydrogen; and $R^2$ is phenyl.

7. The polymerization inhibitor system of claim 2 wherein component (b) is N-phenyl-N-(1,4-dimethylpentyl)-p-phenylenediamine.

8. A composition in accordance with claim 2 wherein the weight ratio of component (a) to component (b) is between about 10:1 and about 1:10.

9. A system in accordance with claim 2 wherein the weight ratio of component (a) to component (b) is between about 4:1 and about 1:4.

10. A polymerization inhibitor system comprising a compound having the structure:

wherein $R^4$ and $R^5$ are both hydrogen, and
   a phenylenediamine of formula II $$\text{II}$$

wherein $R^6$ is $C_6$–$C_{10}$ aryl or $C_7$–$C_{16}$ alkaryl; and $R^7$, $R^8$ and $R^9$ are independently selected from the group consisting of hydrogen, $C_1$–$C_{12}$ alkyl, $C_3$–$C_{12}$ cycloalkyl, $C_7$–$C_{11}$ aralkyl and $C_7$–$C_{16}$ alkaryl.

* * * * *